United States Patent [19]

Minami et al.

[11] Patent Number: 5,767,303

[45] Date of Patent: Jun. 16, 1998

[54] PROCESS OF PRODUCING CARBONIC DIESTER

[75] Inventors: Takeshi Minami, Yokohama; Noriyuki Yoneda, Tokyo; Yoshimi Shiroto; Haruto Kobayashi, both of Yokohama, all of Japan

[73] Assignee: Chiyoda Corporation, Japan

[21] Appl. No.: 876,239

[22] Filed: Jun. 16, 1997

[30] Foreign Application Priority Data

Oct. 4, 1996 [JP] Japan .................................. 8-283022

[51] Int. Cl.$^6$ .................................................. C07C 68/00
[52] U.S. Cl. .......................... 558/275; 558/277; 502/165
[58] Field of Search ........................ 558/275, 277

[56] References Cited

U.S. PATENT DOCUMENTS

| | | | |
|---|---|---|---|
| Re. 29,338 | 8/1977 | Perrotti et al. ................. | 558/275 X |
| 4,370,275 | 1/1983 | Stammann et al. ................. | 558/277 |
| 4,625,044 | 11/1986 | Curnutt ................. | 558/277 |
| 4,761,467 | 8/1988 | Bhattacharya ................. | 558/277 |

*Primary Examiner*—Michael G. Ambrose
*Attorney, Agent, or Firm*—Lorusso & Loud

[57] ABSTRACT

A process for the production of a carbonic diester, wherein an alcohol is reacted in a reaction zone with carbon monoxide and oxygen in the presence of (a) metallic copper or a copper compound, (b) a heterocyclic compound containing one or more nitrogen atoms in the cyclic skeleton and (c) a glycol ether represented by the following formula (I):

$$R^1O-(CHR^2-CH_2O)_n-R^3 \quad (I)$$

wherein $R^1$ stands for an alkyl group having from 1 to 6 carbon atoms, $R^2$ stands for a hydrogen atom or an alkyl group having 1 or 2 carbon atoms, $R^3$ stands for a hydrogen atom or an alkyl group having from 1 to 6 carbon atoms and n is an integer of from 1 to 12.

17 Claims, 5 Drawing Sheets

PROCESS OF PRODUCING CARBONIC DIESTER

BACKGROUND OF THE INVENTION

This invention relates to a process for the production of a carbonic diester.

A carbonic diester such as dimethyl carbonate is useful as a raw material for pharmaceuticals, agricultural chemicals and additives for gasoline (octane boosters) and as a raw material for the production of organic glasses which is a substitute for phosgene.

One conventional method of preparing a carbonic diester includes reacting phosgene with an alcohol. In addition to problems caused by the use of highly toxic phosgene, the conventional method has problems because highly corrosive hydrochloric acid is produced as a by-product.

As a method of preparing dimethyl carbonate without using phosgene, a process employing oxidative carbonylation of methanol using cuprous chloride as a catalyst is known (Quad. Ind. Chim. Ital. vol. 21, No. 1 (1985)). While this method does not use phosgene, hydrochloric acid is formed as a by-product by the contact of cuprous chloride and water. Thus, it is necessary to line the inside walls of the reactor and associated equipments with a glass and, therefore, a large-sized reaction apparatus cannot be utilized. Moreover, since the cuprous chloride catalyst must be used in a large amount in order to obtain a satisfactory reaction rate, the reaction mixture is in the form of a slurry. Therefore, it is necessary to use a specific solid-liquid separation device such as a membrane or a centrifuge in order to recover the ester product from the slurry. This requires significant costs because the device must withstand heat, pressure and hydrochloric acid. To avoid the use of such a specific solid-liquid separation device, a method is proposed in which a dimethyl carbonate product is discharged from the reactor as a gas phase together with a large amount of unreacted raw material gases. This method, however, requires the recycling of the large amount of the unreacted raw material gases to the reactor.

To cope with the problems caused by the use of a slurry reaction system, a method is proposed in which an alcohol is carbonylated using a homogeneous catalyst of copper chloride-nitrogen compound (U.S. Pat. No. Re. 29,338 of Snam Progetti). Because of poor solubility of copper chloride, however, this method is not put into practice. U.S. Pat. No. 4,604,242 (Dow Chemical) suggest the use of a bis(2,4-pentadianato)copper(II)methoxide-pyridine homogeneous catalyst system. This method, however, is not put into practice because the reaction proceeds very slowly and the copper catalyst is not easily available.

As a method of producing a carbonic diester without using a slurry system, a method is also known in which a homogeneous catalyst of $CuCl_2/PdCl_3$ is used (JP-A-5-320098). Because of the use of $PdCl_3$, however, oxalic acid and insoluble copper oxalate are unavoidably formed so that the catalytic activity and selectivity are lowered. Further, a method is proposed in which the oxidative carbonylation is performed in a gas phase using a catalyst having supported thereon a copper salt or a copper complex. For example, U.S. Pat. No. 2,625,044 (Dow Chemical) discloses the use of a catalyst containing copper chloride or copper-pyridine complex supported on activated carbon. This method, however, has a problem because the selectivity to the carbonic diester is low and the catalyst life is not long.

JP-A-6-210181 proposes a method of producing a carbonic diester by oxidative carbonylation of an alcohol in the presence of a catalyst including activated carbon supported thereon a copper-triphenylphosphine complex and a halogen-containing compound. This method has a problem because the catalyst is not able to exhibit constant activity due to a loss of the halogen. The catalyst may be regenerated by treatment with a halogen gas or hydrogen halide. The regeneration treatment, however, causes corrosion of the apparatus, formation of halogenated alkyl as a by-product and/or hydrolysis of the carbonic diester product.

SUMMARY OF THE INVENTION

It is, therefore, an object of the present invention to provide a process which permits the use of a homogeneous catalyst system.

Another object of the present invention is to provide a process which can produce a carbonic diester at a high selectivity and a high reaction rate.

It is a further object of the present invention to provide a process which does not cause corrosion of the apparatus with which the process is performed.

It is yet a further object of the present invention to provide a process in which catalyst inactivation is suppressed.

It is yet a further object of the present invention to provide a homogeneous catalytic composition useful for the production of carbonic diester by oxidative carbonylation of an alcohol.

In accomplishing the foregoing objects, there is provided in accordance with the present invention a process for the production of a carbonic diester, comprising reacting, in a reaction zone, an alcohol with carbon monoxide and oxygen in the presence of ingredient (a) which is metallic copper or a copper compound, ingredient (b) which is a heterocyclic compound containing one or more nitrogen atoms in the cyclic skeleton thereof and ingredient (c) which is a glycol ether represented by the following formula (I):

$$R^1O\text{—}(CHR^2\text{—}CH_2O)_n\text{—}R^3 \qquad (I)$$

wherein $R^1$ stands for an alkyl group having from 1 to 6 carbon atoms, $R^2$ stands for a hydrogen atom or an alkyl group having 1 or 2 carbon atoms, $R^3$ stands for a hydrogen atom or an alkyl group having from 1 to 6 carbon atoms and n is an integer of from 1 to 12.

In another aspect, the present invention provides a catalyst composition in the form of a solution, comprising ingredient (a) which is metallic copper or a copper compound, ingredient (b) which is a heterocyclic compound containing one or more nitrogen atoms in the cyclic skeleton thereof and ingredient (c) which is a glycol ether represented by the following formula (I):

$$R^1O\text{—}(CHR^2\text{—}CH_2O)_n\text{—}R^3 \qquad (I)$$

wherein $R^1$ stands for an alkyl group having from 1 to 6 carbon atoms, $R^2$ stands for a hydrogen atom or an alkyl group having 1 or 2 carbon atoms, $R^3$ stands for a hydrogen atom or an alkyl group having from 1 to 6 carbon atoms and n is an integer of from 1 to 12.

BRIEF DESCRIPTION OF THE DRAWINGS

Other objects, features and advantages of the present invention will become apparent from the detailed description of the invention which follows, when considered in light of the accompanying drawings, in which.

DETAILED DESCRIPTION OF THE PREFERRED EMBODIMENTS OF THE INVENTION

The reaction of an alcohol with oxygen and carbon monoxide which results in the formation of a carbonic diester is as follows:

$2(ROH) + \frac{1}{2}O_2 + 2CuCl \rightarrow 2(CuORCl) + H_2O$ (oxidation)

$2(CuORCl) + CO \rightarrow (RO)_2CO + 2CuCl$ (carbonylation)

$2(ROH) + CO + \frac{1}{2}O_2 \rightarrow (RO)_2CO + H_2O$ (overall)

In the present invention the above oxidative carbonylation reaction is carried out in the presence of ingredient (a) which is metallic copper or a copper compound, ingredient (b) which is a heterocyclic compound containing one or more nitrogen atoms in the cyclic skeleton thereof and ingredient (c) which is a glycol ether represented by the following formula (I):

$$R^1O-(CHR^2-CH_2O)_n-R^3 \quad (I)$$

wherein $R^1$ stands for an alkyl group having from 1 to 6 carbon atoms, $R^2$ stands for a hydrogen atom or an alkyl group having 1 or 2 carbon atoms, $R^3$ stands for a hydrogen atom or an alkyl group having from 1 to 6 carbon atoms and n is an integer of from 1 to 12.

The ingredient (a) serves to function as a catalyst. The copper compound may be, for example, a halide such as a chloride, a bromide or an iodide, e.g. CuCl, CuCl$_2$, CuBr, CuBr$_2$, CuI or CuI$_2$; an inorganic acid salt such as a nitrate, carbonate, borate or phosphate, e.g. Cu(NO$_3$)$_2$, CuB$_4$O$_7$, CuCO$_3$.Cu(OH)$_2$.H$_2$O or CuPO$_4$; an organic salt such as a formate, an acetate or an oxalate, e.g. Cu(HCOO)$_2$, Cu(C$_2$H$_4$) or Cu(CH$_3$COO)$_2$; an oxide such as Cu$_2$O and CuO; a hydroxide such as Cu(OH)$_2$; a complex of the above copper compound with a ligand. The ligand may be, for example, an amine such as trimethylamine, nitrogen-containing heterocyclic compound such as pyridine, or an organic phosphorus compound such as triphenylphosphine. Above all, cuprous chloride (CuCl) and a complex thereof are particularly preferably used as the ingredient (a) for reasons of catalytic activity and selectivity.

The heterocyclic compound containing one or more nitrogen atoms in the cyclic skeleton thereof used as the ingredient (b) may be, for example, a pyridine compound such as pyridine or a substituted pyridine having an inert substituent such as an alkyl group, a hydroxyl group, an alkoxy group or a halogen atom. Illustrative of suitable substituted pyridines are 2-hydroxypyridine, 2-methylpyridine, 2-ethylpyridine, 2,4-dimethylpyridine, 2-methyl-4-hydroxypyridine, 2-hydroxy-4-methoxypyridine and 2-hydroxy-6-chloropyridine. Other examples of the ingredient (b) include phenanthroline compounds, imidazole compounds and dipyridyl compounds. Above all, the use of a pyridine compound, a 2-hydroxypyridine compound, a 2-methylpyridine compound, 1,10-phenanthroline or dipyridyl is particularly preferred. The ingredient (b) and the ingredient (a) form a complex capable of being dissolved in the ingredient (c).

The ingredient (c) is used as a solvent. In the ingredient (c) of the formula (I) above, $R^1$ is an alkyl group having from 1 to 6, preferably 1 to 4, more preferably 1 to 2 carbon atoms, $R^2$ is a hydrogen atom or an alkyl group having 1 or 2 carbon atoms, preferably a hydrogen atom or a methyl group, $R^3$ is a hydrogen atom or an alkyl group having from 1 to 6, preferably 1 to 4, more preferably 1 or 2 carbon atoms and n is an integer of from 1 to 12, preferably 1 to 6, more preferably 2 to 4. When the number of carbon atoms of $R^1$ exceeds 6, when the number of carbon atoms of $R^2$ exceeds 2 or when the number of carbon atoms of $R^3$ exceeds 6, the solubility of the ingredient (a) in the glycol ether is very low. A number of n in excess of 12 is disadvantageous because the solubility of the ingredient (a) in the glycol ether is very low and the viscosity of glycol ether is high. The glycol ethers of the formula (I) may be used singly or as a mixture thereof. The glycol ether of the formula (I) is chemically inert and thermally stable, is not corrosive, does not form precipitates or insoluble matters during the oxidative carbonylation reaction, has a low vapor pressure and can dissolve oxygen, carbon monoxide and the ingredients (a) and (b) therein.

It is preferred that the ingredient (c) be a monoalkyl ether of a glycol obtained by adding 2 to 12 moles of ethylene oxide and/or propylene oxide to 1 mole of methanol, ethanol, propanol and/or butanol or a dialkyl ether of a glycol obtained by substituting the hydrogen atom of the terminal OH group of the above glycol monoalkyl ether with an alkyl group such as methyl, ethyl, propyl or butyl. These glycol ethers can well dissolve carbon monoxide, oxygen and a complex of the ingredients (a) and (b), so that the oxidative carbonylation reaction can proceed in a homogeneous phase without formation of precipitates.

Any alcohol can be used as a raw material for the formation of carbonic diester. Examples of alcohols include saturated or unsaturated aliphatic alcohols having from 1 to 20 carbon atoms such as methanol, ethanol, 1-propanol, 2-propanol, 1-butanol, 1-pentanol, 1-hexanol, 1-octanol, 1-decanol, 1-octadecanol, allyl alcohol, 2-butene-1-ol and 2-hexene-1-ol; alicyclic alcohols having from 3 to 7 carbon atoms such as cyclohexanol and cyclopentanol; aromatic alcohols such as benzyl alcohol and phenethyl alcohol; polyalcohols such as dialcohols, e.g. ethylene glycol, diethylene glycol, triethylene glycol, polyethylene glycol and propylene glycol, and glycerin. Above all, the use of methanol or ethanol is preferred for reasons of a demand for the resulting carbonic diester product.

It is not necessary that carbon monoxide and oxygen used for the oxidative carbonylation reaction have high purity. The carbon monoxide feed and oxygen feed may contain an inert gas such as nitrogen, argon or carbon dioxide. Rather, for the prevention of explosion, it is preferred that the oxygen be diluted with the inert gas, i.e. air can be used as the oxygen feed.

The molar ratio of the ingredient (b) to the ingredient (a) is preferably in the range of 1:10 to 100:1, more preferably 1:2 to 50:1, most preferably 1:1 to 10:1. A molar ratio of the ingredient (b) to the ingredient (a) below 1:10 is disadvantageous because the homogenous catalyst system is not easily obtainable. Too high a ratio in excess of 100:1 is also disadvantageous because the selectivity of carbonic diester based on CO is lowered and the catalyst tends to form precipitates in the presence of the raw material alcohol.

The molar ratio of the ingredient (c) to the ingredient (a) is preferably in the range of 1:2 to 200:1, more preferably 1:1 to 100:1, most preferably 3:1 to 50:1. A molar ratio of the ingredient (c) to the ingredient (a) below 1:2 is disadvantageous because the homogenous catalyst system is not easily obtainable. Too high a ratio in excess of 200:1 is also disadvantageous because the oxidative carbonylation reaction fails to proceed at a satisfactory reaction rate.

The molar ratio of the raw material alcohol to the ingredient (a) is preferably in the range of 3:1 to 700:1, more preferably 30:1 to 500:1, most preferably 50:1 to 300:1. A molar ratio of the alcohol to the ingredient (a) below 3:1 is disadvantageous because the oxidative carbonylation reaction fails to proceed at a satisfactory reaction rate. Too high a ratio in excess of 700:1 is also disadvantageous because the catalyst tends to form precipitates and oxidative carbonylation reaction fails to proceed at a satisfactory reaction rate.

The oxidative carbonylation reaction is preferably performed at a temperature in the range of 30° to 20020 C., more preferably 50°–150° C., most preferably 80°–140° C., under a carbon monoxide partial pressure of in the range of 0.1 to 50 kg/cm$^2$, more preferably 1–30 kg/cm , most preferably 1–25 kg/cm$^2$ and an oxygen partial pressure of in the range of 0.001 to 10 kg/cm$^2$, more preferably 0.005–5 kg/cm$^2$, most preferably 0.01–3 kg/cm$^2$. When the reaction temperature is below 30° C., the reaction fails to proceed at a satisfactory rate. Too high a temperature in excess of 200° C., on the other hand, causes the production of by-products and the decomposition of glycol ether. A carbon monoxide partial pressure below 0.1 kg/cm$^2$ is insufficient to perform the reaction at a satisfactory rate. No additional merits are obtainable when the carbon monoxide partial pressure is higher than 50 kg/cm$^2$. Rather, since it is necessary to use a pressure-resisting reactor, the use of excessively high pressure is disadvantageous from the economic point of view. An oxygen partial pressure below 0.001 kg/cm$^2$ is insufficient to perform the reaction at a satisfactory rate. When the oxygen partial pressure is greater than 10 kg/cm$^2$, on the other hand, glycol ether tends to be oxidized and decomposed and the selectivity of carbonic diester based on CO is lowered.

The process according to the present invention may be carried out in a batch system or in a continuous system.

In a batch system, a raw material alcohol is charged in a reactor together with the above-described ingredients (a), (b) and (c) and, thereafter, carbon monoxide and oxygen are fed to the reactor while maintaining the temperature and the carbon monoxide and oxygen partial pressures at predetermined ranges. The reactor may be, for example, of a stirring-type or of a bubbling-type which can provide sufficient gas-liquid contact. The carbon monoxide and oxygen are fed to the batch-type reactor in an amount of, for example, 8–200 mol/hour (preferably 10–100 mol/hour) and 0.08–4 mol/hour (preferably 0.1–2 mol/hour), respectively, per mole of the copper catalyst, typically CuCl.

In one preferred embodiment, the carbonic diester product may be recovered as a gas phase from the reactor. To the reactor containing remainder liquid phase, the raw material alcohol is again added together with make-up components such as the ingredient (b) and (c) and the process is again started by feeding the carbon monoxide and oxygen to the reactor. Alternatively, the reaction mixture after termination of the reaction is discharged from the reactor and is introduced into a distillation tower to recover the carbonic diester product. The residual fraction containing the ingredients (a), (b) and (c) is recycled to the reactor, to which the raw material alcohol is again added together with make-up components such as the ingredient (b) and (c). The process is again started by feeding the carbon monoxide and oxygen to the reactor. The latter method is more efficient than the former, gas phase recovery method.

In the above embodiment, the oxidation and carbonylation reactions are carried out simultaneously. However, the carbonylation can be preceded by the oxidation, if desired. In this case, the raw material alcohol is charged in the reactor together with ingredients (a), (b) and (c). Then, oxygen is fed to the reactor to provide an oxygen partial pressure of 0.001–10 kg/cm$^2$ and the oxidation is performed at a temperature of 30°–150° C. Thereafter, the remaining oxygen is discharged and carbon monoxide is fed to the reactor to provide a carbon monoxide partial pressure of 0.1–50 kg/cm$^2$. The carbonylation is performed at a temperature of 30°–200° C.

In the continuous-type system, the reactor is first charged with the ingredients (a), (b) and (c). Then, the raw material alcohol, carbon monoxide and oxygen are continuously fed to the reactor while supplying make-up components such as ingredients (b) and (c) and while discharging a portion of the reaction mixture for the recovery of the carbonic diester product. The reactor may be, for example, of a stirring-type or of a bubbling-type which can provide sufficient gas-liquid contact. The reaction mixture may be discharged as a gas phase or liquid phase. In the liquid phase-discharging method, the reaction mixture discharged from the reactor is introduced into a separation zone such as a flusher or a distillation tower to recover the carbonic diester product. The residual fraction containing the ingredients (a), (b) and (c) is continuously recycled to the reactor. The liquid phase-discharging method is more efficient than the gas phase recovery method.

In the continuous process, too, the oxidation and carbonylation can be carried out separately without difficulty, since the catalyst system used in the present invention is stable and homogenous. In such a case, two reactors for use in oxidation and carbonylation, respectively, are connected in series and oxygen and carbon monoxide are respectively supplied to the two reactors. The reaction conditions in the two reactors are similar to those described above in connection with the batch system. The method in which the oxidation and carbonylation are carried out in separate zones has a merit that the formation of an explosive gas mixture containing carbon monoxide and oxygen can be avoided and a loss of carbon monoxide due to combustion with oxygen is minimized.

In the above batch and continuous processes, at least a portion of the reaction mixture comprising the catalyst (ingredient (a)) is discharged from the reactor and introduced into a treatment zone to treat the discharged reaction mixture with carbon monoxide and to regenerate the catalyst. The treated mixture containing the thus regenerated catalyst is recycled to the reactor.

The treatment of the discharged reaction mixture with carbon monoxide is preferably performed under a carbon monoxide partial pressure of at least 0.1 kg/cm$^2$, more preferably 0.5–50 kg/cm$^2$ at a temperature in the range of 50° to 200° C., more preferably 70° to 150° C. A carbon monoxide pressure of less than 0.1 kg/cm$^2$ is insufficient to regenerate the catalyst. No additional merits are obtainable by using a carbon monoxide pressure in excess of 50 kg/cm$^2$. Rather, the use of a high pressure requires the use of a pressure-resisting reactor and is economically disadvantageous. A treatment temperature below 50° C. is insufficient to regenerate the catalyst. When the temperature is higher than 200° C., the glycol ether (ingredient (c)) tends to be decomposed.

Figure 1:
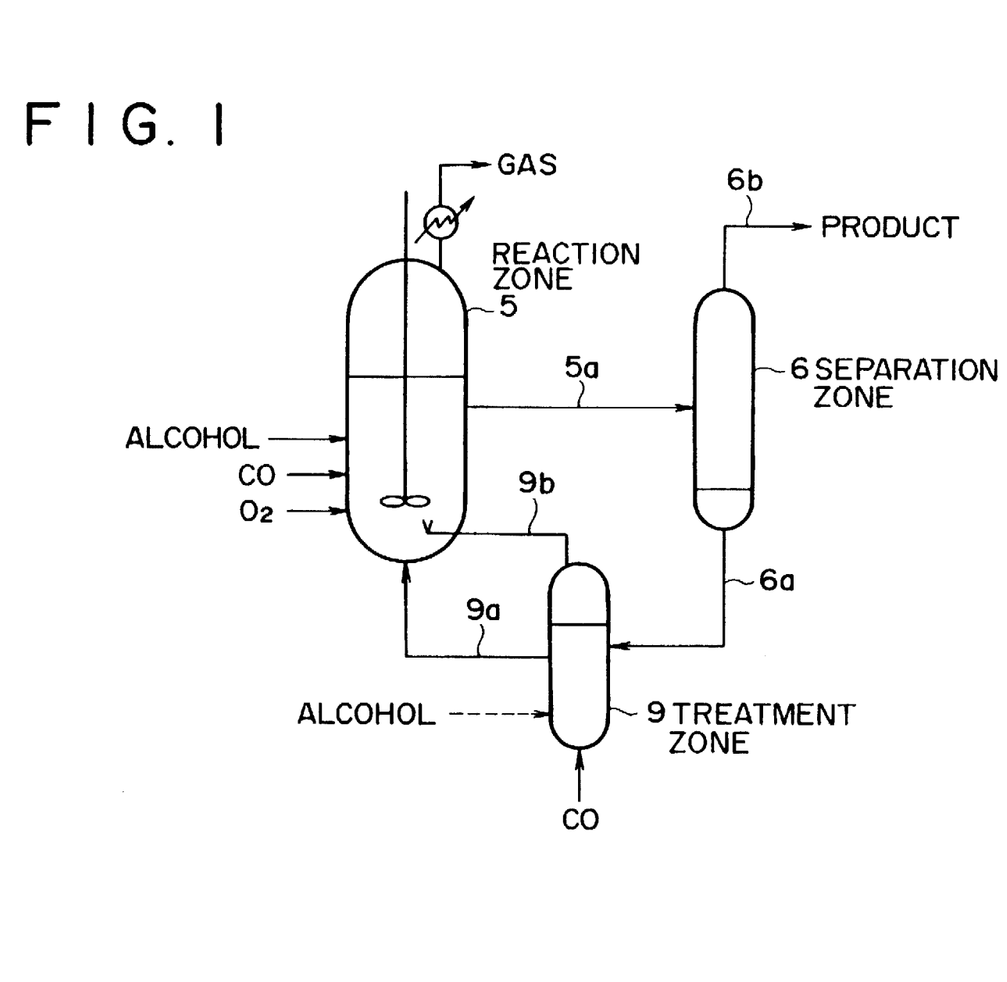
FIG. 1 is a diagrammatic illustration of one embodiment of an apparatus for carrying out the process according to the present invention.

The process according to the present invention will now be described with reference to the drawings which schematically show apparatuses useful for carrying out the process. Referring first to FIG. 1, designated as 5 is a reaction zone which is a stirring-type reactor having a lower portion to which feed lines for a raw material alcohol, carbon monoxide and oxygen are connected. The reactor 5 is adapted to contain the above-described ingredients (a), (b) and (c) such that the raw material alcohol is reacted with carbon monoxide and oxygen in the presence of the ingredients (a), (b) and (c). Connected to the reactor 5 by a line 5a is a separation zone 6, such as a flusher, for receiving a portion of the reaction mixture in the reactor 5 and for separating a carbonic diester product from the reaction mixture. In a case where methanol is used as the raw material alcohol, the product contains an azeotropic mixture of dimethyl carbonate with methanol, an azeotropic mixture of dimethyl carbonate with water and unreacted methanol. The product is discharged overhead from the separation zone 6 through a line 6b. Designated as 9 is a treatment zone connected to a bottom of the flusher 6 through a line 6a for receiving a portion of the residue containing the catalyst system (ingredient (a) complexed with ingredient (b)). Carbon monoxide is fed to the treatment zone 9 to regenerate the catalyst. The regenerated catalyst and excess carbon monoxide are introduced into the reactor 5 through lines 9a and 9b, respectively. If desired, the raw material alcohol may be fed to the treatment zone 9 rather than to the reactor 5. The above process is suitably carried out in a continuous manner. It is also possible to use a single device for carrying out both the separation of the product and the regeneration of the catalyst.

Figure 2:
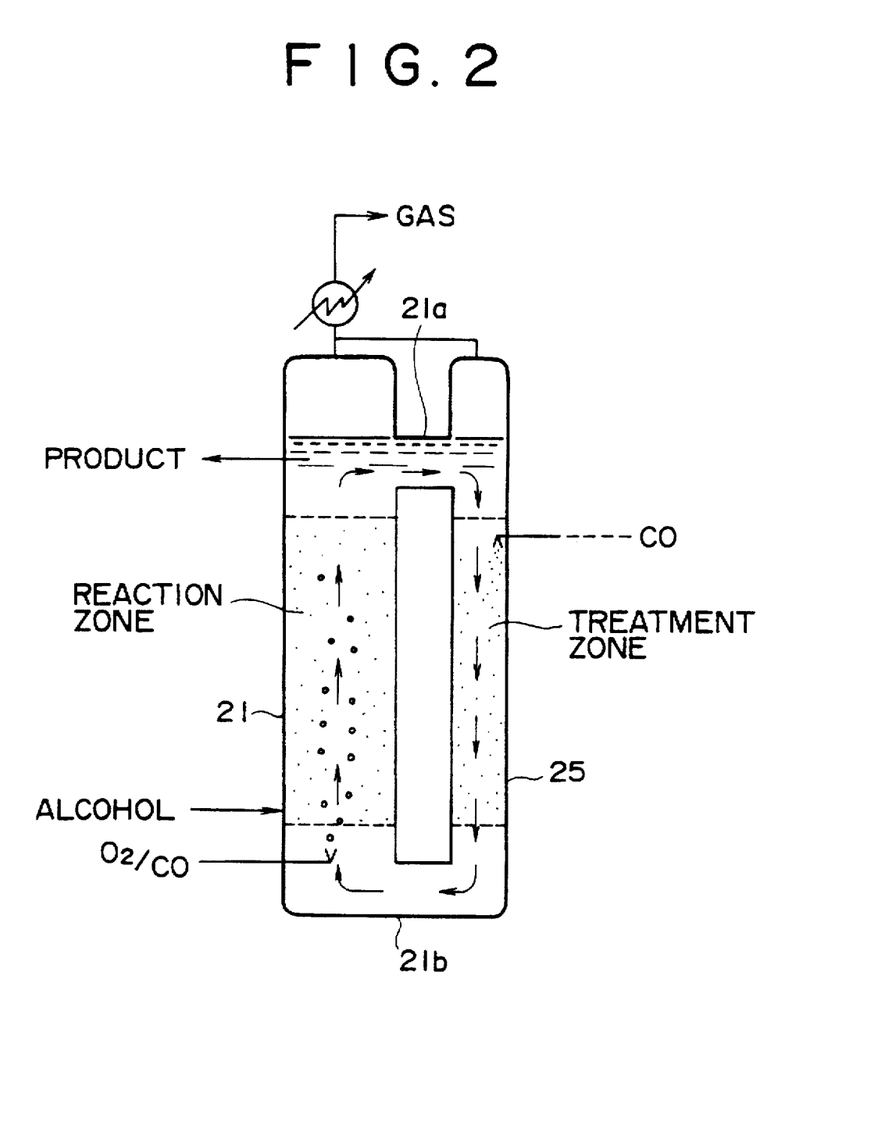
FIG. 2 is a diagrammatic illustration of another embodiment of an apparatus for carrying out the process according to the present invention.

FIG. 2 shows another embodiment of an apparatus for carrying out the process according to the present invention. The apparatus is of a bubbling reactor type and includes first and second, juxtaposed, vertically extending cylindrical vessels 21 and 25, respectively, which are connected at both top portions and bottom portions by pipes 21a and 21b, respectively to form a loop.

The first vessel 21 has a lower portion to which feed lines for a raw material alcohol, carbon monoxide and oxygen are connected. The amount of the carbon monoxide fed from the lower end portion of the first cylindrical vessel 21 is stoichiometrically in excess. The first and second vessels 21 and 25 are adapted to contain a reaction mixture containing the above-described ingredients (a), (b) and (c). By feeding CO and O2 to the bottom of the first vessel 21, a stream which flows upward through the first cylindrical vessel 21 and downward through the second cylindrical vessel 25 is occurred due to the difference in density between the liquid in the first vessel 21 and the liquid in the second vessel 25.

Thus, the raw material alcohol is reacted with carbon monoxide and oxygen in the presence of the ingredients (a), (b) and (c) in the first vessel 21. Namely, a reaction zone is formed in the first vessel 21. The reaction mixture after passage through the reaction zone is then streamed through the upper pipe 21a into the second vessel 25. Since the reaction mixture still contains carbon monoxide though oxygen has been consumed in the reaction zone, the catalyst (ingredient (a)) is regenerated by the carbon monoxide during the passage of the reaction mixture through the second vessel 25. Namely, a treatment zone for regenerating the catalyst is formed in the second vessel 25.

The regenerated catalyst-containing mixture is then recycled through the lower pipe 21b to the first vessel 21. If desired, a small amount of carbon monoxide may be fed to an upper portion of the second vessel 25 to facilitate the catalyst regeneration. The above process is carried out in a continuous manner.

Figure 3:
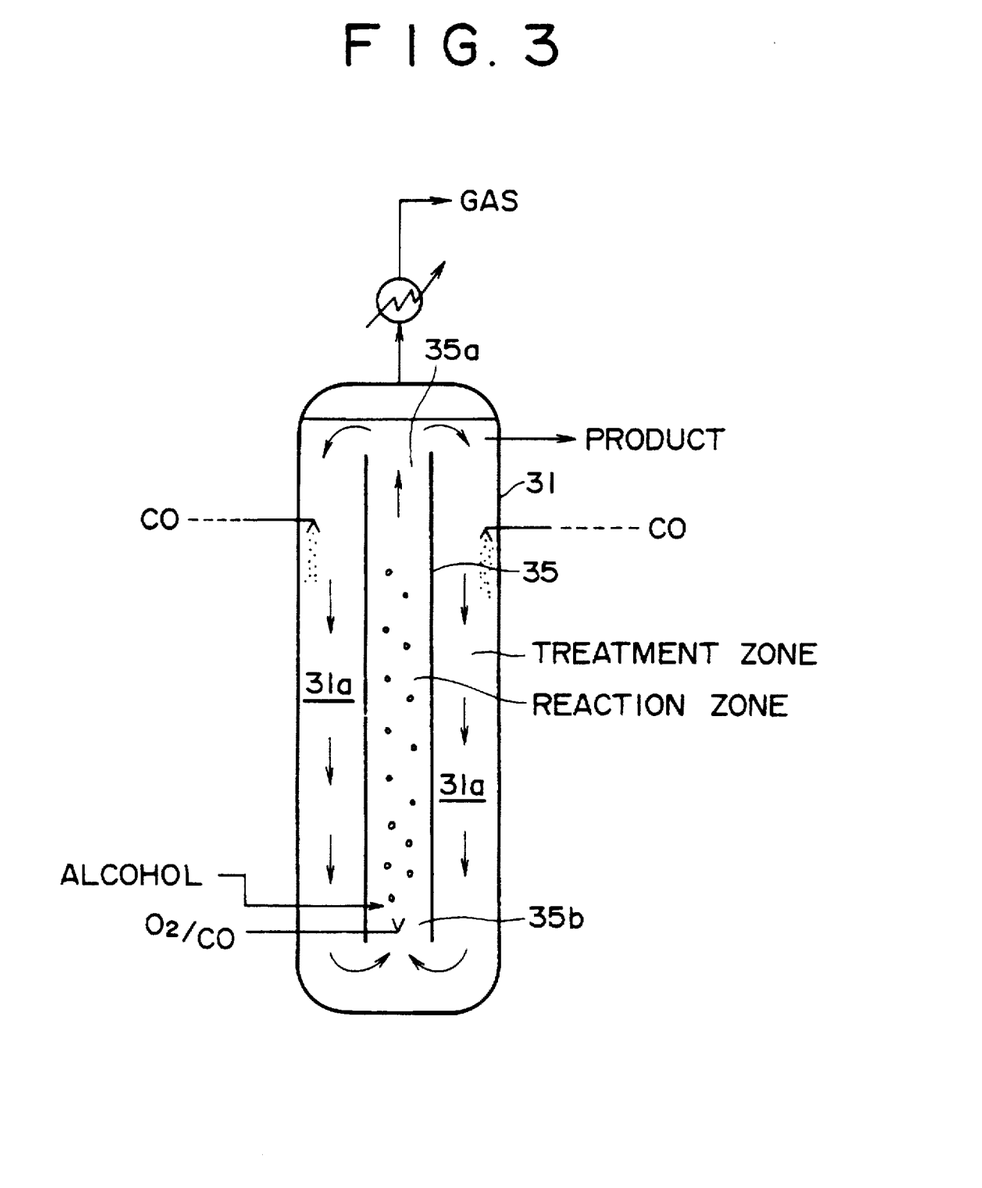
FIG. 3 is a diagrammatic illustration of a further embodiment of an apparatus for carrying out the process according to the present invention.

FIG. 3 shows a further embodiment of an apparatus, so called draft tube type reactor, for carrying out the process according to the present invention. The apparatus is of a bubbling reactor type and includes an outer vertically extending cylindrical vessel 31 closed in both top and bottom thereof. An inner, vertically extending cylindrical member 35 is coaxially disposed within the outer vessel 31 to define an annular space 31a therebetween. The inner cylindrical member (draft tube) 35 is open in both top 35a and bottom 35b thereof so that the inside space thereof is in fluid communication with the annular space 31a.

The inner cylindrical member 35 has a lower portion to which feed lines for a raw material alcohol, carbon monoxide and oxygen are connected. The amount of the carbon monoxide fed from the lower end portion of the inner cylindrical member 35 is stoichiometrically in excess. The vessels 31 is adapted to contain a reaction mixture containing the above-described ingredients (a), (b) and (c). By feeding carbon monoxide and oxygen to the bottom of the inner cylindrical member 35, there is established a circulating stream of the reaction mixture that flows upward through the inner cylindrical member 35 and downward through the annular space 31a.

Thus, the raw material alcohol is reacted with carbon monoxide and oxygen in the presence of the ingredients (a), (b) and (c) in the inner cylindrical member 35. Namely, a reaction zone is formed in the inner cylindrical member 35. The reaction mixture after passage through the reaction zone is then streamed through the upper opening 35a into the annular space 31a. Since the reaction mixture still contains carbon monoxide though oxygen has been consumed in the reaction zone, the catalyst (ingredient (a)) is regenerated by the carbon monoxide during the passage of the reaction mixture through the annular space 31a. Namely, a treatment zone for regenerating the catalyst is formed in the annular space 31a.

The regenerated catalyst-containing mixture is then recycled through the lower opening 35b to the inner cylindrical member 35. If desired, carbon monoxide may be fed to an upper portion of the annular space 31a to facilitate the catalyst regeneration. The above process is carried out in a continuous manner. The apparatuses shown in FIGS. 2 and 3 do not require a stirrer and are simple in structure and, therefore, are advantageous from the standpoint of economy. Further, the apparatuses which are columnar can be easily constructed into a large-sized structure.

The following examples will further illustrate the present invention.

EXAMPLE 1

Preparation of Homogeneous Catalyst System

In a 200 ml erlenmeyer flask equipped with a screw cap, 31.4 g of pyridine were charged. Then, with stirring using a magnetic stirrer, 13.5 g of CuCl were gradually added into the flask. Immediately after completion of the addition of CuCl, 77.3 g of triethylene glycol dimethyl ether (HISOLVE MTM manufactured by Toho Chemical Industry Inc.) were further added to the flask. Since a small amount of precipitates were formed, the mixture within the flask was heated to about 50° C. with stirring to form a homogenous catalyst solution. Then, 57.1 g of methanol were added to the flask to obtain a raw material mixture in the form of a dark green homogeneous solution.

Preparation of Dimethyl Carbonate in Batch System

The raw material mixture obtained above was charged in a 300 ml autoclave (made of Hastelloy C) and the atmosphere within the autoclave was purged with a Co gas. The autoclave was then pressurized with a CO gas to 25 kg/cm². With stirring at agitation speed of 1,000 r.p.m., the solution was heated to 130° C. and, thereafter, a CO gas and an $O_2$ gas were fed to the autoclave at feed rates of 1.25 mol/hour and 0.1 mol/hour, respectively, while maintaining the autoclave at 130° C. The reaction was continued for 5 hours. The gas chromatographic analysis revealed that dimethyl carbonate was produced in an amount of 30.9 g. The copper utilization rate UC was found to be 561%, the methanol-based selectivity SM to be 80% and the CO-based selectivity SC to be 60% (2 hours after start of the reaction) and 40% (4 hours after start of the reaction). The copper utilization rate UC, methanol-based selectivity SM and CO-based selectivity SC are as defined below:

$$UC=Y\times 2/W\times 100(\%)$$

where Y represents the yield (mol) of dimethyl carbonate and W represents the amount (mol) of CuCl used;

$$SM=Y\times 2/M\times 100(\%)$$

where Y is as defined above and M represents the amount (mol) of methanol consumed;

$$SC=Y/C\times 100$$

where Y is as defined above and C represents the amount (mol) of Co consumed.

COMPARATIVE EXAMPLE 1

Preparation of Slurry Catalyst

In a 300 ml erlenmeyer flask equipped with a screw cap, 134 g of methanol were charged. Then, with stirring using a magnetic stirrer, 26.8 g of CuCl were gradually added into the flask. The mixture in the flask was further stirred with heating up to about 50° C. using a far infrared heater. The CuCl failed to be dissolved in methanol so that a slurry was formed.

Preparation of Dimethyl Carbonate

The slurry obtained above was charged in a 300 ml autoclave (made of Hastelloy C) and the atmosphere within the autoclave was purged with a CO gas. The autoclave was then pressurized with a CO gas to 25 kg/cm²G. With stirring at agitation speed of 1,000 r.p.m., the solution was heated to 130° C. and, thereafter, a CO gas and an $O_2$ gas were fed to the autoclave at feed rates of 1.25 mol/hour and 0.1 mol/ hour, respectively, while maintaining the autoclave at 130° C. The reaction was continued for 5 hours. The gas chromatographic analysis revealed that dimethyl carbonate was produced in an amount of 31.3 g. The copper utilization rate UC was found to be 257%, the methanol-based selectivity SM to be 90% and the CO-based selectivity SC to be 90% (2 hours after start of the reaction) and 55% (4 hours after start of the reaction). The inside wall of the reactor after reaction was found to lost the gloss and to be corroded by contact with the reaction mixture.

EXAMPLE 2

Figure 4:
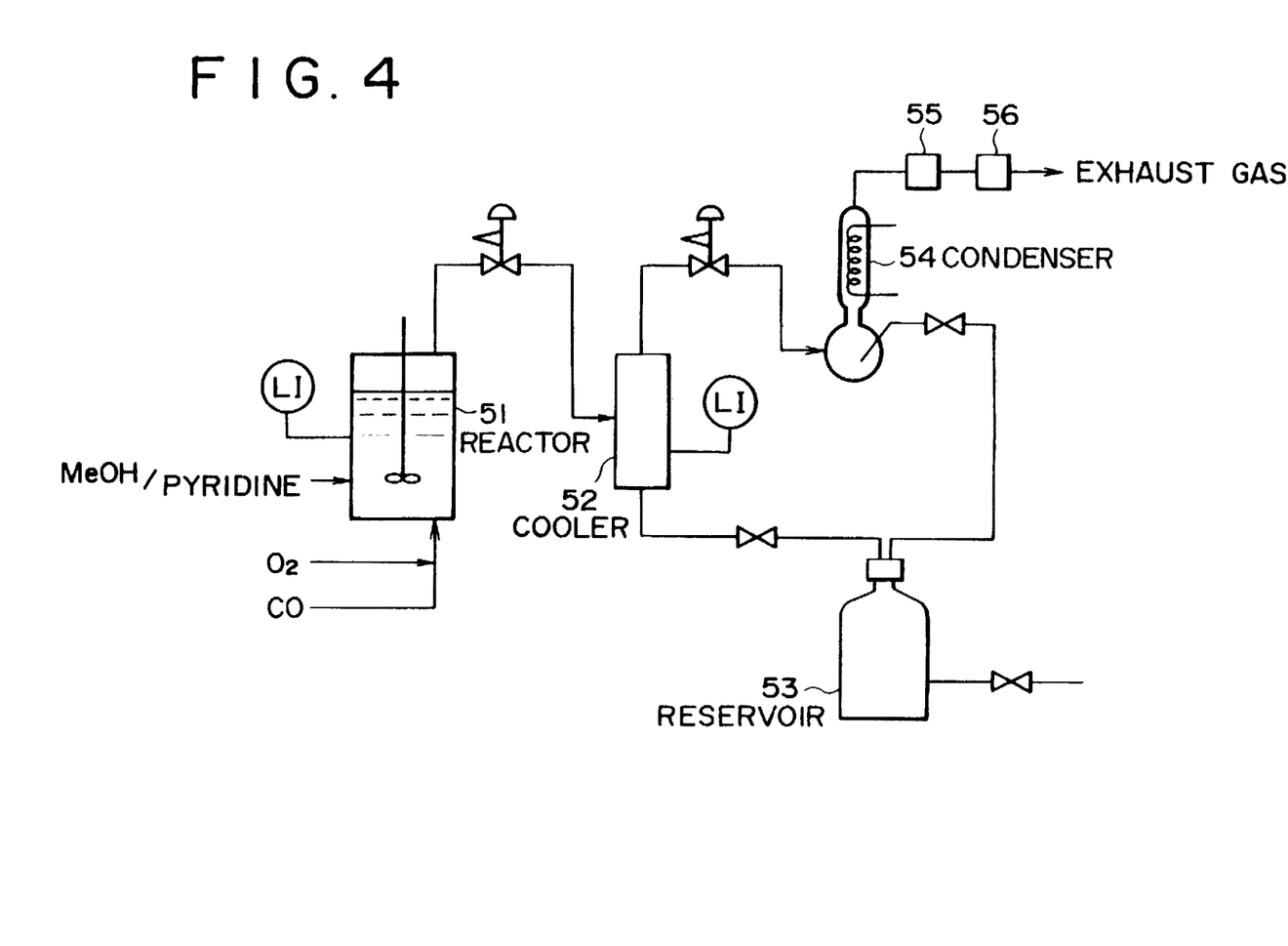
FIG. 4 is a diagrammatic illustration of an apparatus used in Example 2.

Dimethyl carbonate was prepared using an apparatus illustrated in FIG. 4. A raw material liquid (200 ml) prepared in the same manner as that in Example 1 and containing 1.3% by weight of CuCl, 2.9% by weight of pyridine, 49.6% by weight of triethylene glycol dimethyl ether and 46.2% by weight of methanol was charged in a reactor 51 (made of Hastelloy C). With stirring at 1,000 r.p.m., the liquid in the reactor 51 was heated to 100° C. while feeding a CO gas at a rate of 1.25 mol/hour. The reactor 51 was then pressurized with a CO gas to 25 kg/cm². An $O_2$ gas was fed at a rate 0.1 mol/hour and methanol containing 0.5% by weight of pyridine was fed at a rate so that the liquid level in the reactor was maintained at a predetermined level. A vapor phase containing dimethyl carbonate, methanol, water and pyridine was emitted overhead from the reactor 51 and introduced into a cooler 52 maintained at 10° C. and 1 kg/cm²G to recover these components as liquid. The recovered liquid was collected in a reservoir 53. A non-condensed gas was discharged from the cooler 52 and introduced into a condenser 54 to separate the non-condensed gas into liquid and gas phases. The liquid phase was collected in the reservoir 53 while the gas phase was passed through an $O_2$ meter 55 and a gas meter 56 and discharged as an exhaust gas. After 0.5, 1, 2, 3 and 4 hours from the commencement of the reaction, the exhaust gas was analyzed by gas chromatography to measure the concentrations of $CO_2$, CO, dimethyl carbonate, methanol and $O_2$. Also measured at the above points in time were the amounts of methanol, pyridine, triethylene glycol dimethyl ether and dimethyl carbonate by gas chromatography and the amount of water by the Karl Fischer's method in the liquid phase recovered in the reservoir 53. From the results of the measurement, CO-based selectivity (SC2) and methanol-based selectivity (SM) were calculated as follows:

$$SC2=[1-2V/(WF-WE)]\times 100$$

wherein SC2 represents the CO-based selectivity (%), V represents the concentration (% by volume) of $CO_2$ in the exhaust gas, WF represents the concentration (% by volume) of $O_2$ in the raw material feed and WE represents the concentration (% by volume) of $O_2$ in the exhaust gas; and $$SM=Y\times 2/M\times 100$$

wherein SM represents the methanol-based selectivity (%), Y represents the yield (mol) of dimethyl carbonate and M represents the amount (mol) of methanol consumed. The results are summarized in Table 1. The yield of dimethyl carbonate throughout 4 hours reaction was found to be 0.59 mol/hour.liter. No other by-products than $CO_2$ were detected.

TABLE 1

| Change in Selectivity (SC2 and SM) with Time | | | | | |
|---|---|---|---|---|---|
| Time (hour) | 0.5 | 1 | 2 | 3 | 4 |
| SC2 (%) | 83 | 77 | 78 | 72 | 59 |
| SM (%) | 92 | 99 | 100 | 100 | 100 |

EXAMPLE 3

Preparation of Dimethyl Carbonate in Batch System

In this example, the oxidation and carbonylation are performed separately in this order. The dark green solution obtained in the same manner as that in Example 1 was charged in a 300 ml autoclave (made of Hastelloy C) and the atmosphere within the autoclave was purged with an $O_2$ gas. With stirring at agitation speed of 1,400 r.p.m., the solution was heated to 70° C. The autoclave was then pressurized with an $O_2$ gas to 4 kg/cm² to start the oxidation of methanol while maintaining the temperature at 70° C. After two hours reaction, the heating was stopped to permit the temperature to be lowered to 40° C. The pressure within the autoclave was then released and the atmosphere within the autoclave was purged with a CO gas. With stirring at agitation speed of 1,400 r.p.m., the solution was heated to 120° C. Thereafter, a CO gas was fed to the autoclave so that the pressure in the autoclave was increased to 25 kg/cm². The carbonylation was thus performed for 2 hours, while maintaining the autoclave at 120° C. The heating was then stopped to permit the temperature to be lowered to 40° C. The reaction mixture in the autoclave was sampled and measured for the yield of dimethyl carbonate. 3.8 Grams of dimethyl carbonate were produced. The selectivity of dimethyl carbonate based on CO (produced dimethyl carbonate (mol)/consumed CO (mol) was 76%. No corrosion of the inside wall of the reactor was observed.

COMPARATIVE EXAMPLE 2

Preparation of Slurry Catalyst

In a 200 ml erlenmeyer flask equipped with a screw cap, 19 g of pyridine were charged. Then, with stirring using a magnetic stirrer, 24 g of CuCl were gradually added into the flask. After dissolution of CuCl in pyridine, 120 g of methanol was added so that a slurry was formed. The mixture in the flask was further stirred with heating up to about 50° C. using a far infrared heater but the solid matters were not dissolved.

Preparation of Dimethyl Carbonate

The slurry obtained above was charged in a 300 ml autoclave (made of Hastelloy C) and the atmosphere within the autoclave was purged with an $O_2$ gas. With stirring at agitation speed of 1,400 r.p.m., the slurry was heated to 70° C. The autoclave was then pressurized with an $O_2$ gas to 4 kg/cm² to start the oxidation of methanol while maintaining the temperature at 70° C. After 45 minutes reaction, the heating was stopped to permit the temperature to be lowered to 40° C. The pressure within the autoclave was then released and the atmosphere within the autoclave was purged with a CO gas. With stirring at agitation speed of 1,400 r.p.m., the solution was heated to 120° C. Thereafter, a CO gas was fed to the autoclave so that the pressure in the autoclave was increased to 25 kg/cm². The carbonylation was thus performed for 45 minutes, while maintaining the autoclave at 120° C. The heating was then stopped to permit the temperature to be lowered to 40° C. The analysis of the reaction mixture revealed the production of dimethyl carbonate. However, about 80% of the reaction mixture is in the form of a gel and, therefore, this process is ill-suited for industrial applications.

EXAMPLES 4 TO 8

Example 1 was repeated in the same manner as described except that the raw material mixture had a composition shown in Table 2. The yield of dimethyl carbonate (DMC) was shown in Table 2.

TABLE 2

| Example | 4 | 5 | 6 | 7 | 8 |
|---|---|---|---|---|---|
| Composition (g) | | | | | |
| CuCl | 3.38 | 3.38 | 3.38 | 3.38 | 3.38 |
| TGDE*1 | 77.3 | 77.3 | 77.3 | 77.3 | 77.3 |
| Methanol | 57.1 | 57.1 | 57.1 | 57.1 | 57.1 |
| Pyridine | 7.9 | — | — | — | — |
| 2-Hydroxypyridine | — | 9.4 | — | — | — |
| 2-Methylpyridine | — | — | 9.4 | — | — |
| 2,2'-Dipyridyl | — | — | — | 8.0 | — |
| 1,10-Phenanthroline | — | — | — | — | 9.2 |
| Yield of DMC (g) | 28.0 | 6.0 | 20.0 | 23.0 | 19.9 |

*1: Triethylene glycol dimethyl ether

EXAMPLES 9 TO 13

Example 1 was repeated in the same manner as described except that the raw material mixture had a composition shown in Table 3. The yield of dimethyl carbonate (DMC) was shown in Table 3 together with the results in Example 4.

TABLE 3

| Example | 4 | 9 | 10 | 11 | 12 | 13 |
|---|---|---|---|---|---|---|
| Composition (g) | | | | | | |
| CuCl | 3.38 | 3.38 | 3.38 | 3.38 | 3.38 | 3.38 |
| Pyridine | 7.8 | 7.8 | 7.8 | 7.8 | 7.8 | 7.8 |
| Methanol | 57.1 | 57.1 | 57.1 | 57.1 | 57.1 | 57.1 |
| TGDE*1 | 77.3 | | | | | |
| EGPE*2 | | 77.3 | | | | |
| TGME*3 | | | 77.3 | | | |
| PGME*4 | | | | 77.3 | | |
| DGBE*5 | | | | | 77.3 | |
| TEGL*6 | | | | | | 77.3 |
| Yield of DMC (g) | 28.0 | 20.1 | 22.1 | 28.0 | 22.4 | 15.6 |

*1: Triethylene glycol dimethyl ether
*2: Ethylene glycol monophenyl ether
*3: Triethylene glycol monomethyl ether
*4: Propylene glycol monomethyl ether
*5: Diethylene glycol monobutyl ether
*6: Triethylene glycol

EXAMPLE 14

In a 500 ml vessel, 114.2 g of methanol, 7.85 g of pyridine, 77.3 g of triethylene glycol dimethyl ether were placed, to which 3.85 g of CuCl were gradually added. With stirring at 50° C. the mixture in the vessel was stirred to obtain a raw material solution. The raw material solution was then charged in a 300 ml autoclave (made of titanium) and the atmosphere within the autoclave was purged with a CO gas. The autoclave was then pressurized with a CO gas to 25 kg/cm². With stirring at agitation speed of 1,000 r.p.m., the solution was heated to 100° C. and, thereafter, a CO gas and an $O_2$ gas were continuously fed to the autoclave at feed rates of 1.25 mol/hour and 0.1 mol/hour, respectively, while maintaining the autoclave at 100° C. The reaction was continued for 3 hours. The reaction liquid after 3 hours reaction and the exhaust gas after 1, 2 and 3 hours from the commencement of the reaction were analyzed by gas chromatography for the measurement of the amount of dimethyl carbonate in the reaction mixture and the concentrations of oxygen and carbon dioxide (by-product) in the exhaust gas. Dimethyl carbonate was produced in an amount of 44 g. The methanol-based selectivity SM was found to be 98% and the CO-based selectivity SC to be 78% (1 hour after start of the reaction) and 68% (3 hours after start of the reaction).

The reaction liquid remaining after 3 hours reaction was placed in a rotary evaporator for removing the residual methanol, dimethyl carbonated produced, water and a portion of pyridine to obtain a residual solution containing the copper catalyst. The residual solution was mixed with fresh methanol and pyridine to obtain a mixture having a composition similar to the above raw material solution. This mixture was charged in the 300 ml autoclave and the atmosphere within the autoclave was purged with a CO gas. The autoclave was then pressurized with a CO gas to 25 kg/cm². With stirring at agitation speed of 1,000 r.p.m., the solution was heated to 100° C. and maintained at that temperature for 30 minutes to regenerate the catalyst. Thereafter, a CO gas and an $O_2$ gas were continuously fed to the autoclave at feed rates of 1.25 mol/hour and 0.1 mol/hour, respectively, while maintaining the autoclave at 100° C. and 25 kg/cm². The reaction was continued for 3 hours. The reaction liquid after 3 hours reaction and the exhaust gas after 1, 2 and 3 hours from the commencement of the reaction were analyzed by gas chromatography for the measurement of the amount of dimethyl carbonate in the reaction mixture and the concentrations of oxygen and carbon dioxide in the exhaust gas.

The foregoing process including the regeneration and oxidative carbonylation was repeated three times. The yield of dimethyl carbonate and CO-based selectivity SC2 at 1 and 3 hours reaction at respective first through third cycles are summarized in Table 4. Throughout the operations, no corrosion of the inside wall of the reactor was observed.

TABLE 4

| Repeated Cycle | First | Second | Third |
| --- | --- | --- | --- |
| Yield of Dimethyl Carbonate (g) | 44.3 | 44.8 | 42.5 |
| Selectivity SC2 (%) | | | |
| After 1 hour | 78 | 80 | 74 |
| After 3 hour | 68 | 60 | 59 |

EXAMPLE 15

Figure 5:
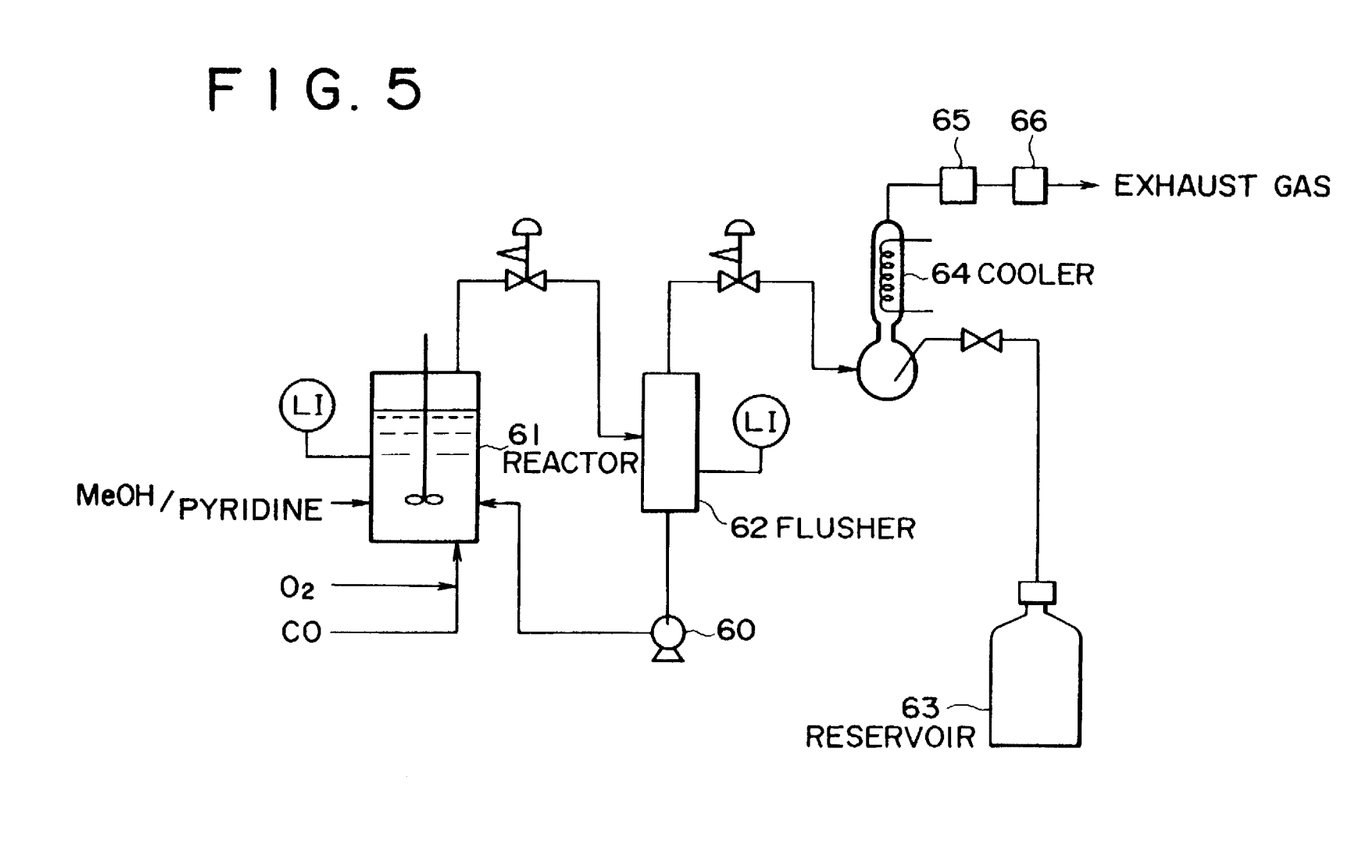
FIG. 5 is a diagrammatic illustration of an apparatus used in Example 15.

Dimethyl carbonate was continuously prepared using an apparatus illustrated in FIG. 5. A raw material liquid (300 ml) prepared in the same manner as that in Example 1 and containing 1.7% by weight of CuCl, 3.9% by weight of pyridine, 38.1% by weight of triethylene glycol dimethyl ether and 56.3% by weight of methanol was charged in a reactor 61 (made of Hastelloy C) and a flusher 62. With stirring at 1,000 r.p.m., the liquid in the reactor 61 and flusher 62 was heated to 100° C. while feeding a Co gas at a rate of 1.25 mol/hour. The reactor 61 was then pressurized with a Co gas to 25 kg/cm²G. The flusher 62 was maintained at 0.8 kg/cm². An $O_2$ gas was fed at a rate 0.1 mol/hour and methanol containing 0.75% by weight of pyridine was fed at a rate so that the liquid level in the flusher 62 was maintained at a predetermined level (in the range of 1.5 to 2.5 mol/ minute) . The reaction mixture in a mixed gas and liquid phase was discharged from the reactor 61 and introduced into the flusher 62 where the reaction mixture was separated into a gas phase containing dimethyl carbonate, methanol, pyridine, water and triethylene glycol dimethyl ether and a liquid phase. The liquid phase was recycled to the reactor 61 by a recycle pump 60 at a rate of 8 ml/minute. The gas phase was fed to a cooler 64 to recover the dimethyl carbonate and other components as a condensed liquid in a reservoir 63. The non-condensed vapor phase was passed through an $O_2$ meter 65 and a gas meter 66 and discharged as an exhaust gas. Since most of the $O_2$ fed to the reactor 61 was consumed therein, the atmosphere within the flusher 62 consisted essentially of CO, so that the catalyst was effectively regenerated in the flusher 62. During the continuous operation, the exhaust gas and the recovered condensed liquid were occasionally analyzed for the calculation of selectivity and yield in the same manner as that in Example 2. The results are summarized in Table 5.

TABLE 5

| Time (hour) | Selectivity (%) SC2 | Selectivity (%) SM | Yield of DMC (mol/liter · hour) | $O_2$ in Exhaust Gas (mol %) |
| --- | --- | --- | --- | --- |
| 1 | 88 | 103 | — | 0.48 |
| 2 | 79 | 100 | — | 0.20 |
| 4 | 75 | 100 | 0.67 | 0.11 |
| 6 | 73 | 102 | 0.77 | 0.09 |
| 8 | 76 | 99.5 | 0.75 | 0.14 |
| 12 | 77 | 97.3 | 0.79 | 0.45 |
| 16 | 78 | 98.9 | 0.70 | 0.18 |
| 22 | 78 | 102 | 0.73 | 0.18 |
| 23 | 79 | 101 | 0.70 | 0.25 |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A process for the production of a carbonic diester, comprising reacting, in a reaction zone, an alcohol with carbon monoxide and oxygen in the presence of ingredient (a) which is metallic copper or a copper compound, ingredient (b) which is a heterocyclic compound containing one or more nitrogen atoms in the cyclic skeleton thereof and ingredient (c) which is a glycol ether represented by the following formula (I):

$$R^1O-(CHR^2-CH_2O)_n-R^3 \qquad (I)$$

wherein $R^1$ stands for an alkyl group having from 1 to 6 carbon atoms, $R^2$ stands for a hydrogen atom or an alkyl group having 1 or 2 carbon atoms, $R^3$ stands for a hydrogen atom or an alkyl group having from 1 to 6 carbon atoms and n is an integer of from 1 to 12.

2. A process as claimed in claim 1, wherein said ingredient (b) is selected from the group consisting of pyridine, 2,2'-dipyridyl and 1,10-phenanthroline.

3. A process as claimed in claim 1, wherein the molar ratio of said ingredient (b) to said ingredient (a) is in the range of 1:10 to 100:1.

4. A process as claimed in claim 1, wherein the molar ratio of said ingredient (c) to said ingredient (a) is in the range of 1:2 to 200:1.

5. A process as claimed in claim 1, wherein said reaction is performed under an oxygen partial pressure of in the range of 0.001 to 10 kg/cm².

6. A process as claimed in claim 1, wherein said reaction is performed under a carbon monoxide partial pressure of in the range of 0.1 to 50 kg/cm¹.

7. A process as claimed in claim 1, wherein said reaction is performed at a temperature in the range of 30° to 200° C.

8. A process as claimed in claim 1, further comprising the steps of:

discharging at least a portion of the reaction mixture comprising said ingredient (a) from said reaction zone;

introducing said discharged reaction mixture into a treatment zone to treat said discharged reaction mixture with carbon monoxide and to regenerate said ingredient (a), thereby obtaining a treated mixture containing said regenerated ingredient (a); and recycling at least a portion of said treated mixture to said reaction zone.

9. A process as claimed in claim 8, wherein said treatment of said discharged reaction mixture with carbon monoxide is performed under a carbon monoxide partial pressure of at least 1.0 kg/cm$^2$.

10. A process as claimed in claim 8, wherein said treatment of said discharged reaction mixture with carbon monoxide is performed at a temperature in the range of 50° to 200° C.

11. A process as claimed in claim 8, further comprising separating said discharged reaction mixture into a carbonic ester-containing portion and an ingredient (a)-containing portion, and introducing said ingredient (a)-containing portion to said treatment zone.

12. A process as claimed in claim 8, wherein said reaction zone and said treating zone are provided within first and second, juxtaposed, vertically extending cylindrical vessels, respectively, with said first and second cylindrical vessels being connected at both top portions and bottom portions to form a loop; and wherein said carbon monoxide and oxygen used in said reaction zone are fed from a lower end portion of said first cylindrical vessel and directed upward to establish a circulating stream of said reaction mixture within said loop that flows upward through said first cylindrical vessel and downward through said second cylindrical vessel.

13. A process as claimed in claim 12, wherein the amount of said carbon monoxide fed from said lower end portion of said first cylindrical vessel is stoichiometrically in excess.

14. A process as claimed in claim 12, wherein a carbon monoxide gas is fed from an upper end portion of said second cylindrical vessel and directed downward for use in said treatment zone.

15. A process as claimed in claim 8, wherein said reaction zone is provided within a first vertically extending cylindrical vessel and said treatment zone is provided within an annular space defined between said first cylindrical vessel and a second vertically extending cylindrical vessel coaxially disposed outside said first cylindrical vessel; and wherein said carbon monoxide and oxygen used in said reaction zone are fed from a lower end portion of said first cylindrical vessel and directed upward to establish such a circulating stream of said reaction mixture that flows upward through said first cylindrical vessel and downward through said annular space.

16. A process as claimed in claim 15, wherein the amount of said carbon monoxide fed from said lower end portion of said first cylindrical vessel is stoichiometrically in excess.

17. A process as claimed in claim 15, wherein a carbon monoxide gas is fed from an upper end portion of said annular space and directed downward for use in said treatment zone.

* * * * *

UNITED STATES PATENT AND TRADEMARK OFFICE
CERTIFICATE OF CORRECTION

PATENT NO. : 5,767,303
DATED : June 16, 1998
INVENTOR(S) : MINAMI et al

It is certified that error appears in the above-indentified patent and that said Letters Patent is hereby corrected as shown below:

Col. 5, line 18, "20020" should read --200°--.

Col. 14, line 63, "kg/cm$^1$" should read --kg/cm$^2$--.

Signed and Sealed this

Second Day of March, 1999

Attest:

Q. TODD DICKINSON

*Attesting Officer*     Acting Commissioner of Patents and Trademarks